United States Patent
Vogt et al.

(10) Patent No.: US 10,086,343 B2
(45) Date of Patent: Oct. 2, 2018

(54) STORAGE AND MIXING SYSTEM FOR PASTY CEMENT COMPONENTS AND METHOD THEREFOR

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 0 days.

(21) Appl. No.: 15/447,193

(22) Filed: Mar. 2, 2017

(65) Prior Publication Data
US 2017/0252715 A1    Sep. 7, 2017

(30) Foreign Application Priority Data
Mar. 3, 2016   (DE) .................... 10 2016 103 816

(51) Int. Cl.
*B01F 15/00*   (2006.01)
*A61B 17/88*   (2006.01)
(Continued)

(52) U.S. Cl.
CPC ...... *B01F 15/0087* (2013.01); *A61B 17/8805* (2013.01); *A61B 17/8825* (2013.01);
(Continued)

(58) Field of Classification Search
CPC ............... B01F 15/0097; B01F 3/10; B01F 2215/0039; B01F 5/244; B01F 15/0215;
(Continued)

(56) References Cited

U.S. PATENT DOCUMENTS 2,446,501 A    8/1948  Weber
3,370,754 A *  2/1968  Schumann .......... A61C 9/0026
                                                222/132
(Continued)

FOREIGN PATENT DOCUMENTS

DE    25 21 392 A1   11/1976
DE    18 14 845 U1    9/1978
(Continued)

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.
(Continued)

*Primary Examiner* — Vishal Pancholi
(74) *Attorney, Agent, or Firm* — Norris McLaughlin & Marcus P.A.

(57) ABSTRACT

A storage and mixing system for pasty two-component polymethyl methacrylate bone cements comprises a tubular cartridge having a cylindrical inner chamber, a dispensing plunger that is axially displaceable in the inner chamber of the cartridge, a partition disposed axially in the tubular cartridge, and a cartridge head which closes one end of the tubular cartridge. The cartridge head has a slot-shaped opening, wherein the partition protrudes from the inner chamber of the cartridge through the slot-shaped opening of the cartridge head, wherein the partition divides the cylindrical inner chamber of the cartridge bounded by the dispensing plunger and the cartridge head into two cavities that are spatially separated from one another. A first pasty cement component is present in the first cavity and a second pasty cement component is present in the separate second cavity, wherein the partition is removable through the slot-shaped opening of the cartridge head so that the two separate
(Continued)

cavities are connected to one another after the partition is removed.

25 Claims, 11 Drawing Sheets

(51) Int. Cl.
*B01F 5/00* (2006.01)
*B05C 17/01* (2006.01)
*B01F 3/10* (2006.01)
*B01F 3/08* (2006.01)
*B01F 5/06* (2006.01)
*B01F 15/02* (2006.01)
*B05C 17/005* (2006.01)

(52) U.S. Cl.
CPC ........ *A61B 17/8833* (2013.01); *B01F 3/0861* (2013.01); *B01F 3/10* (2013.01); *B01F 5/00* (2013.01); *B01F 5/0614* (2013.01); *B01F 15/00506* (2013.01); *B01F 15/0215* (2013.01); *B01F 15/0237* (2013.01); *B05C 17/00506* (2013.01); *B05C 17/00559* (2013.01); *B05C 17/00593* (2013.01); *B05C 17/00596* (2013.01); *B05C 17/0106* (2013.01); *A61B 2017/8838* (2013.01); *B01F 2215/0029* (2013.01); *B01F 2215/0431* (2013.01)

(58) Field of Classification Search
CPC .. A61B 17/8805; A61B 17/8833; B65D 81/32
USPC .............................. 222/137, 145.6, 386, 391
See application file for complete search history.

(56) References Cited

U.S. PATENT DOCUMENTS

| | | | | |
|---|---|---|---|---|
| 3,730,394 | A * | 5/1973 | Woodson | B01F 13/002 |
| | | | | 222/137 |
| 3,815,878 | A * | 6/1974 | Baskas | A61C 9/0026 |
| | | | | 206/219 |
| 5,082,147 | A * | 1/1992 | Jacobs | B05C 17/00509 |
| | | | | 222/137 |
| 5,405,056 | A * | 4/1995 | Mills | B05B 7/2467 |
| | | | | 222/136 |
| 5,501,371 | A * | 3/1996 | Schwartz-Feldman | |
| | | | | A61C 9/0026 |
| | | | | 222/136 |
| 6,302,574 | B1 | 10/2001 | Chan | |
| 6,935,541 | B1 | 8/2005 | Campbell et al. | |
| 6,938,797 | B2 | 9/2005 | Brugner et al. | |
| 7,793,800 | B2 * | 9/2010 | Griesbaum | B05C 17/00559 |
| | | | | 222/137 |
| 8,960,501 | B2 * | 2/2015 | Pappalardo | B01F 5/0082 |
| | | | | 222/145.5 |
| 8,986,313 | B2 | 3/2015 | Vogt et al. | |
| 9,522,368 | B2 * | 12/2016 | Bublewitz | A61M 5/31596 |
| 2004/0074927 | A1 | 4/2004 | Lafond | |
| 2004/0129122 | A1 | 7/2004 | Brugner et al. | |
| 2009/0105144 | A1 | 4/2009 | Vogt et al. | |
| 2009/0105366 | A1 | 4/2009 | Vogt et al. | |
| 2011/0084094 | A1 | 4/2011 | Reidt et al. | |
| 2015/0182925 | A1 * | 7/2015 | Tartler | B01F 7/002 |
| | | | | 366/247 |

FOREIGN PATENT DOCUMENTS

| | | |
|---|---|---|
| DE | 103 37 790 A1 | 3/2005 |
| DE | 202005010206 U1 | 9/2005 |
| DE | 102007052116 A1 | 4/2009 |
| DE | 102007050762 B3 | 5/2009 |
| DE | 102008030312 A1 | 1/2010 |
| EP | 0 119 847 A2 | 9/1984 |
| EP | 1 392 450 B1 | 7/2005 |
| JP | 2007-502241 A | 2/2007 |
| JP | 2013-138845 A | 7/2013 |

OTHER PUBLICATIONS

Australian Office Action for corresponding Australian application No. 2017201447 dated May 17, 2018.
English Translation Office Action for corresponding Japanese application No. 2017-035000 dated Apr. 3, 2018.

* cited by examiner

STORAGE AND MIXING SYSTEM FOR PASTY CEMENT COMPONENTS AND METHOD THEREFOR

This application claims foreign priority benefit under 35 U.S.C. 119 of German Application No. DE 10 2016 103 816.4 filed Mar. 3, 2016.

DESCRIPTION OF THE DISCLOSURE

The invention relates to a storage and mixing system for pasty two-component polymethyl methacrylate bone cements, the storage and mixing system comprising a tubular cartridge having a cylindrical inner chamber and a dispensing plunger that is axially displaceable in the inner chamber of the cartridge.

The invention also relates to a method for mixing pasty cement components of a cement dough, and in particular of a pasty polymethyl methacrylate bone cement, using such a storage and mixing system.

The subject matter of the invention is thus a simple storage and mixing system for pasty two-component polymethyl methacrylate bone cement, which is cost-effective to produce and can be used to mix and dispense the highly viscous, pasty components of the polymethyl methacrylate bone cement using manually operable dispensing devices.

Conventional polymethyl methacrylate bone cements (PMMA bone cements) are composed of a powder component and a liquid monomer component (K.-D. Kühn: Knochenzemente für die Endoprothetik: Ein aktueller Vergleich der physikalischen and chemischen Eigenschaften handelsüblicher PMMA-Zemente (Bone Cements for Endoprostheses: A Current Comparison of the Physical and Chemical Properties of Commercially Available PMMA Cements). Springer-Verlag Berlin Heidelberg New York, 2001). After the cement powder has been mixed with the liquid monomer component, these polymethyl methacrylate bone cements are applied while still in an uncured, pasty state in the form of a cement dough. When mixing systems are used, the cement dough is present in a cartridge in the case of powder/liquid cements. The cement dough is pushed out of this cartridge by the movement of a dispensing plunger. The dispensing plungers usually have a diameter between 30 mm and 40 mm and thus have a surface area of 7.0 $cm^2$ to 12.5 $cm^2$ on the outer side on which the pusher of the dispensing device engages during the process of pressing out. The movement of the dispensing plunger is effectuated by manually operable mechanical dispensing devices, which are also referred to as applicators. These dispensing devices or applicators normally have a pressing force in the range of approximately 1.5 kN to 3.5 kN.

Pasty two-component bone cements, as they are known from DE 10 2007 050 762 B3, DE 10 2008 030 312 A1 and DE 10 2007 052 116 B4, for example, constitute a more recent development. In the case of these two-component bone cements, two pasty cement components are stored in two separate cartridges comprising two separate dispensing plungers. During the application, the two pastes are pressed out of the cartridges and into a static mixer by the movement of the dispensing plunger, and are dispensed through a dispensing tube after having been mixed. A suitable composition of the pasty cement components immediately yields a cement dough that is dry to the touch and ready to be applied after the two cement components have been mixed. This eliminates waiting periods until the non-tacky state of the cement dough is reached, which necessarily occur with existing conventional polymethyl methacrylate bone cements all the time. As a result, valuable time is saved in the operating room.

Experiments conducted by the inventors within the scope of the present invention showed that the drop in pressure at the static mixer in the dispensing tube is very high during the pressing process of the cartridges due to the high viscosity of the pasty cement components. Experiments conducted by the inventors also showed that a pressing force of greater than 7 kN is needed when using a conical dispensing tube having an overall length of approximately 17 cm and an inside diameter of 11 mm at the cartridge head, and when using ten static mixing elements, in order to press out the highly viscous cement pastes at a dispensing rate acceptable for the medical user.

When existing, conventional PMMA bone cements, which are composed of a liquid monomer component and a cement powder component stored separately therefrom, are applied, the created cement dough is pressed out with the aid of manually operable dispensing devices after the two cement components have been mixed in cementing systems or vacuum cementing systems. These simple mechanical dispensing devices use in particular clamping rods for pressing, which are driven by a manually actuatable rocker lever. The manually driven dispensing devices have been tried and tested around the globe for decades and so far, represent the prior art. The advantage of these dispensing devices is that the medical user, by way of the manual force to be applied, has a feel for the penetration resistance of the bone cement dough in the bone structures (spongiosa).

When highly viscous pasty cement components are used with cartridges, in which the dispensing plungers on the outer plunger sides on which the pushers of the dispensing devices engage have a total surface area in the range of 7.0 $cm^2$ to 12.5 $cm^2$, these devices cannot be operated manually or only with very high force expenditure. This high force expenditure cannot be expected of medical users in the operating room.

Electrically driven pressing devices are also known from the adhesives and sealants field. These devices can be driven either by rechargeable batteries and batteries, or with the aid of a stationary power supply unit. These devices, some of which have very high pressing forces, are able to press out particularly viscous, pasty compounds. The disadvantage of using electric motors, however, is that these contain non-ferrous metals and are expensive to procure. Such devices require complex sterilization, or even replacement, in the operating area, which must be kept in a sterile condition. If electrical wiring is present, the movement of the user in the operating room may be impeded.

Moreover, pneumatic devices have been proposed. These devices require a stationary or mobile compressed air connection (U.S. Pat. No. 2,446,501 A; DE 20 2005 010 206 U1). This necessitates air hoses, which can impede the movement of the user.

As an alternative, it is also possible to use compressed gas cartridges to provide compressed gas. For this purpose, devices have been proposed in which the compressed gas supply is controlled by a valve, and additionally the flow of the viscous compound is controlled by a second valve (US 2004/0074927 A1; U.S. Pat. No. 6,935,541 B1). In these devices, the gas cartridges are integrated in the devices. Such systems connected to compressed air or compressed gas cartridges always necessitate a compressed gas source, without which the systems cannot be used.

Thus, it is the object of the invention to overcome the drawbacks of the prior art. In particular, a simple storage and mixing system for pasty two-component polymethyl methacrylate bone cements which is inexpensive to produce and a method for producing a bone cement using a storage and mixing system are to be provided, wherein the storage and mixing system is operational as a single-use, ready-to-use system in the simplest manner within just a few seconds, requiring a minimal number of assembly steps, and, after being connected to manually drivable medical dispensing devices or applicators, generates a homogeneously mixed cement dough immediately after the manual actuation of the dispensing device has begun, and dispenses this at the dispensing opening of a dispensing tube. The manually operable dispensing devices used previously in operating rooms for conventional polymethyl methacrylate bone cements, which each comprise a push rod and a plate, are to be used to dispense the two-component polymethyl methacrylate bone cement, or the cement dough, using the storage and mixing system to be developed. This is intended to avoid the procurement of special dispensing devices for dispensing pasty two-component polymethyl methacrylate bone cements.

The storage and mixing system to be developed should preferably not necessitate two push rods that are connected to one another and that are to be advanced synchronously, so that the entire device is not significantly longer and larger than the mixing systems, and vacuum mixing systems, previously customary for conventional powder/liquid polymethyl methacrylate bone cements. A simple solution is to be found, which allows two pasty cement components to be driven from the device synchronously and manually by way of only a push rod and a plate attached thereto. The pasty cement components of the bone cement are to be stored separately from one another reliably within the storage and mixing system. For use, it should be possible to reliably combine the two pasty cement components. The storage and mixing system is also to be able to dispense a small volume of the homogeneously mixed cement dough of approximately 50 ml, and of no more than 70 ml, without leaving larger residual amounts (more than 10 ml) behind in the system and requiring complex disposal. Larger volumes of the cement dough are not sought. The described small amounts are sufficient for many applications, such as surgeries in the knee area.

The transition from the cartridge to the dispensing tube is preferably to be designed such that the flow resistance of the pasty cement components is as low as possible when these are pressed out. The cement components used must be pasty cement components that can be applied directly after being pressed out, which is to say which require no time for swelling of the PMMA bone cement. The device is to be configured such that the design, to as great an extent as possible, precludes the user from confusing the relevant assembly steps, and that the storage and mixing system can also be employed by substantially untrained staff. Furthermore, a method for mixing the pasty cement components and for dispensing the homogeneously mixed cement dough is to be provided.

The objects of the invention are achieved by a storage and mixing system for pasty two-component polymethyl methacrylate bone cements, the storage and mixing system comprising:
a) a tubular cartridge having a cylindrical inner chamber;
b) a dispensing plunger that is axially displaceable in the inner chamber of the cartridge;
c) a partition disposed axially in the tubular cartridge;
d) a cartridge head, which closes one end of the tubular cartridge, wherein the cartridge head has a slot-shaped opening, wherein the partition protrudes from the inner chamber of the cartridge through the slot-shaped opening of the cartridge head, wherein the partition divides the cylindrical inner chamber of the cartridge bounded by the dispensing plunger and the cartridge head into two cavities that are spatially separated from one another, wherein a first pasty cement component is present in the first cavity and a second pasty cement component is present in the separate second cavity, and wherein the partition is removeable (by pulling it out) through the slot-shaped opening of the cartridge head so that the two separate cavities are connected to one another after the partition is removed.

According to the invention, a cylindrical geometry, or a cylindrical inner chamber, shall be understood to mean a general cylindrical shape having any arbitrary basic shape, which is to say not only cylinders having a circular base area. The cylindrical inner chamber thus does not have to have any cylindrical base areas. However, an inner chamber having a perpendicular circular cylindrical geometry is preferred according to the invention since the storage and mixing system can then be produced in the simplest, particularly cost-effective manner, and is not prone to malfunctions during use. For example, jamming of the dispensing plunger cannot occur easily.

According to a preferred embodiment of the storage and mixing system according to the invention, a securing element can be provided, which must be released before the partition is removable or can be pulled out of the inner chamber through the slot-shaped opening.

Preferably, it may be provided that the two cavities have the same or approximately the same volumes. It is particularly preferred if the volumes of the two cavities deviate less than 20% from one another.

The pasty two-component polymethyl methacrylate bone cement can be produced by mixing the first pasty cement component with the second pasty cement component.

It may be provided on the storage and mixing systems according to the invention that the dispensing plunger is disposed at the end opposite the cartridge head in the inner chamber of the cartridge.

In this way, it is possible to attach a dispensing tube to the cartridge at the cartridge head, or instead of the cartridge head, through which the two pasty cement components of the PMMA bone cement can be driven from the inner chamber of the cartridge by advancing the dispensing plunger into the dispensing tube.

It may also be provided that the storage and mixing system comprises a dispensing tube, on which a fastening means for fastening to the cartridge is provided, wherein the dispensing tube instead of the cartridge head is preferably to be fastened to the cartridge.

The fastening means is preferably an internal thread, which can be screwed onto an external thread on the cartridge. The external thread on the cartridge is particularly preferably also used to detachably fasten the cartridge head to the cartridge.

According to the invention, a static mixer is preferably disposed in the dispensing tube. The invention also proposes that a static mixer be disposed in the dispensing tube, and that an internal thread, an external thread, elements of a bayonet catch and/or detent elements of a detent closure be attached to the base of the dispensing tube as connecting means.

In this way, the dispensing tube can be used to mix the cement components and apply these with pinpoint precision.

A longer dispensing tube is advantageous especially for applying a PMMA bone cement to sites that are difficult to access.

In the case of storage and mixing systems comprising a dispensing tube, it may be provided that the ratio of the diameter of the inner chamber of the cartridge to the inside diameter of the dispensing tube is smaller than 5 to 2, wherein the ratio of the diameter of the inner chamber of the cartridge to the inside diameter of the dispensing tube is preferably smaller than or equal to 2 to 1, and especially particularly preferably the ratio of the diameter of the inner chamber of the cartridge to the inside diameter of the dispensing tube is 8 to 5.

In this way, it is achieved that a sufficient flow velocity of the PMMA bone cement is achieved at the dispensing opening of the dispensing tube during the advancement of the dispensing plunger.

It may be provided that the diameter of the inner chamber of the cartridge is smaller than or equal to 25 mm, wherein the diameter of the inner chamber of the cartridge is preferably smaller than or equal to 20 mm.

In the case of storage and mixing systems comprising a dispensing tube, it may also be provided the diameter of the inner chamber of the cartridge is smaller than or equal to 25 mm, and the inside diameter of the dispensing tube is smaller than or equal to 15 mm, wherein the diameter of the inner chamber of the cartridge is preferably smaller than or equal to 20 mm, and the inside diameter of the dispensing tube is smaller than or equal to 12 mm.

As a result of the composition of the cartridge, or of the cartridge and of the dispensing tube, according to the invention, it is possible to accommodate both pasty cement components of the PMMA bone cement in a single cartridge, which still allows pressing by way of a manual force application, however which, at the same time, can still be loaded using conventional techniques. With larger diameters, manual force application is no longer readily sufficient for pressing the viscous cement components of the bone cement out of the cartridge.

In one refinement of the invention, it is proposed for the ratio of the diameter of the inner chamber of the cartridge to the distance between the dispensing plunger and the cartridge head to be smaller than or equal to 1 to 4, wherein the ratio of the diameter of the inner chamber of the cartridge to the distance between the dispensing head and the cartridge head is preferably smaller than or equal to 1 to 10.

In a preferred refinement of the storage and mixing system according to the invention, it is proposed that the slot-shaped opening is shaped to match the cross-section of the partition.

It is thus achieved that residue of the cement components adhering to the partition are scraped off and do not find their way into the surrounding area. This prevents the operating room from being contaminated with the cement components. Moreover, the partition is thus guided in a stable manner when it is pulled out of the inner chamber.

According to the invention, it may be provided that the first pasty cement component and the second pasty cement component are in contact with one another after the partition has been pulled out.

It is thus achieved that the pasty cement components of the PMMA bone cement are present inside the inner chamber of the cartridge, which is then shared, after the partition has been pulled out, and can be driven out of the inner chamber together, wherein the mixing of the two cement components can already start in the inner chamber of the cartridge.

It is also proposed for the storage and mixing system to comprise at least two guide elements, which are disposed parallel to the longitudinal axis of the cartridge in or on the inside wall of the cartridge, wherein the partition is guided by the at least two guide elements, the partition preferably engages in the at least two guide elements in a form-locked manner and/or the dispensing plunger comprises a guide element, into which the partition is pushed or inserted, on the end face delimiting the inner chamber.

It is also possible to provide more than two guide elements.

In this way, better sealing of the two cavities separated by the partition can be achieved. Moreover, the partition is thus guided when it is being pulled out, or the arrangement of the partition in the inner chamber is thus defined.

In the case of storage and mixing systems comprising guide elements, it may be provided that axial recesses are present on the inner side of the cartridge, serving as guide elements, and/or that a linear recess is present on the side of the dispensing plunger facing the cartridge head, serving as a guide element, wherein the ends of the linear recesses are preferably aligned with one another at the axial recesses of the cartridge.

It is particularly preferred if the axial recesses are implemented by grooves.

Alternatively, it may be provided that axial ribs are present on the inner side of the cartridge, serving as guide elements, and/or that a rib is present on the side of the dispensing plunger facing the cartridge head, wherein the ends of the rib on the dispensing plunger are preferably aligned with one another at the axial ribs of the cartridge.

With these two variants, a simple composition of the guide elements and a sufficiently tight connection between the guide elements or the inside wall of the cartridge and the partition is achieved. In this way, the cement components are storable in a stable manner in the cartridge even over an extended time.

Even if the guide elements break the cylinder geometry, the inner chamber of the cartridge is still regarded as cylindrical within the meaning of the present invention. Preferably, however, the guide elements do not break the cylinder geometry, but only the rotational symmetry of the inner chamber by being provided as linear structures on the lateral surface of the cylindrical inner chamber parallel to the cylinder axis.

According to a preferred refinement of the present invention, it may be provided that an axial movement of the dispensing plunger in the direction of the cartridge head is blocked by the partition when the partition spatially divides the inner chamber of the cartridge into the two cavities.

This ensures that the two cement components of the PMMA bone cement can only be driven from the cartridge after the partition has been removed, whereby application errors are avoided.

It is furthermore proposed within the scope of the present invention that two passages be provided in the cartridge head, which connect the two cavities to the surrounding area of the storage and mixing system, wherein a plug is disposed in each of the passages, wherein the plugs preferably comprise a detent element on the side of the plug facing the inner chamber of the cartridge.

In this way, the cavities can be loaded with the cement components through the passages. After loading, the passages can be closed with the aid of the plugs, and particularly preferably based on the detent elements such that these can no longer be readily detached from the cartridge head, and thus close the cartridge in a tight manner.

The plugs and the passages preferably have the cross-sectional shape of a half moon, circle, or segment of a circle.

So as to increase the maximum possible storage duration of the cement components in the storage and mixing system, it may be provided that the partition, on the edge to the connection to the inside wall of the cartridge, comprises at least one peripheral rubber-elastic seal and/or has a widening to achieve sealing with the inside wall of the cartridge across a larger surface area.

In this way, better sealing of the two separate cavities from one another is achieved, and a premature reaction of the cement components during storage is prevented. The partition preferably has a plate-shaped design.

Furthermore, it may preferably be provided that a loading plunger is disposed in each of the cavities, the plungers being axially movable in the cavities, wherein the loading plungers are preferably connected or connectable to the dispensing plunger by way of a detent means, wherein particularly preferably two mating detent means and at least one vent hole are provided in the dispensing plunger, through which air trapped between the loading plunger and the dispensing plunger can escape from the cavities.

The loading plungers can be used to load the cavities with the cement components. The cement components are pressed into the cavities, and in the process the loading plungers are pushed in the direction of the dispensing plunger, without leaving undesirable trapped air behind in the inner chamber of the cavities, which would interfere with driving the cement components out of the cavities by way of the dispensing plunger. The detent means are used to connect the loading plungers to the dispensing plunger and to prevent these from tilting when the partition is being pulled out, which could then become jammed in the inner chamber of the cartridge, thereby blocking the movement of the dispensing plunger. As an alternative, a suitable positive fit may also be provided between the loading plungers and the dispensing plunger. The at least one vent hole is preferably closed by the loading plungers when these are seated against the dispensing plunger.

Preferred embodiments of the present invention can be characterized in that the partition separates the inner chamber of the cartridge in a manner impervious to liquid, and the two cavities are thus separated from one another in a manner impervious to liquid.

It is thus ensured that the two cement components can also be stored over an extended period in the storage and mixing system, or inside the cartridge. It shall be prevented that the liquid monomer component creeps into the neighboring cavity and reacts with the other cement component.

It may be provided that the cartridge, the cartridge head, the partition and the dispensing plunger are made of plastic material, wherein preferred plastic materials are polyethylene co-vinyl alcohol (EVOH), polybutylene terephthalate (PBT), polyethylene terephthalate (PET), and polymethylmethacrylate-co-acrylonitrile.

The composition by way of plastic materials can be implemented in a cost-effective and simple manner. Due to the resistance of the preferred plastic materials to the chemicals present in the cement components, these are particularly well-suited.

Furthermore, it may be provided that the cartridge head is composed with a rubber-elastic plate and a safety cap, wherein the safety cap blocks a movement of the rubber-elastic plate away from the cartridge with the aid of a protruding rim, and wherein the slot-shaped opening extends through the rubber-elastic plate, wherein the slot-shaped opening preferably divides the rubber-elastic plate into two surface areas, wherein particularly preferably a passage, which is closed by a plug, is provided in each of the two surface areas.

In this way, a good sealing action of the storage and mixing system is achieved. The division of the rubber-elastic plate into two surface areas shall not be understood to mean that the rubber-elastic plate has to comprise two separate parts. The two parts can thus be contiguous and implemented by a single-piece rubber-elastic plate.

It may also be provided that the cartridge head additionally comprises a plastic plate through which the slot-shaped opening extends, wherein the slot-shaped opening divides the plastic plate into two surface areas, wherein an opening is provided in each of the two surface areas, the openings being closed by plugs, wherein the plastic plate is disposed on or beneath the rubber-elastic plate in the cartridge head.

Furthermore, it may be provided that a safety cap is present as a connecting element for connecting the cartridge head to the cartridge, wherein the safety cap comprises an internal thread or an external thread or a bayonet catch or detent elements.

The safety cap is preferably a union nut and is screwable onto the cartridge. The safety cap can be considered to be part of the cartridge head. In this way, the cartridge head is connectable to the cartridge in a stable manner. The safety cap is reliably connectable to the cartridge by way of the connecting element. This reliably prevents a detachment of the cartridge head from the cartridge during storage and transport.

In one refinement of the present invention, it is proposed that the partition, in the region located outside the inner chamber and outside the cartridge head, comprises at least one fastening means for a pulling device for removing the partition from the cartridge.

The partition can thus be removed more easily. The fastening means is preferably a detent tongue, which engages or is able to engage in a mating detent means of the pulling device. A T-shaped handle, a ball-shaped handle or a bean-shaped handle may be disposed or fastened to this fastening means, serving as the pulling device.

It may furthermore be provided that the end face of the cartridge is designed as a cartridge head, comprising at least one slot-shaped opening that divides the end face into two surface areas, wherein an opening, which is closed by a plug, is preferably provided in each of the two surface areas.

For easier usability of the storage and mixing system, it may be provided that a cap is disposed on the cartridge head, wherein the upper end of the cap is designed as a handle, and wherein a connecting element is or detent elements are disposed at the lower rim of the cap, which connects or connect the cap to the cartridge head in a reversibly detachable manner, wherein a fastening element, which is irreversibly connected or is irreversibly connectable to a fastening element of the partition, is attached to the inner side of the cap.

The partition can thus be easily and conveniently manually removed or pulled out of the cartridge using the handle.

It may be provided that the cap is hollow and surrounds the cartridge head.

Preferably, it may be provided that the cartridge comprises a fastening element for a press-out device at one end, and an external thread or an internal thread or an element of a bayonet catch or a detent element of a detent closure as a connecting element at the opposite end.

The objects underlying the present invention are also achieved by a method for mixing pasty cement components of a pasty cement dough, and in particular of a polymethyl methacrylate bone cement, using such a storage and mixing system, comprising the following steps taking place consecutively:

a) pulling the partition out of the cartridge through the cartridge head, whereby the two cavities are connected to one another;
b) removing the cartridge head from the cartridge, or removing at least two plugs from at least two passages in the cartridge head, whereby the cartridge is opened;
c) placing on and connecting a dispensing tube to the opened cartridge, wherein the dispensing tube comprises a mixer;
d) inserting the cartridge into an applicator;
e) pressing out the pasty cement components with the aid of the applicator by axially moving the dispensing plunger in the direction of the dispensing tube, wherein the two cement components are mixed by the mixer in the dispensing tube to yield the pasty cement dough; and
f) pressing the mixed pasty cement dough out of a dispensing opening of the dispensing tube.

It may be provided that a connecting element, which connects the cartridge head to the cartridge, is detached so as to remove the cartridge head from the cartridge in step b).

In this way, a more stable connection is achieved between the cartridge head and the cartridge. Moreover, the counterpiece on the cartridge, which is to say a connecting means on the cartridge, can also be used to connect the dispensing tube.

Furthermore, it may be provided that the dispensing tube is connected to the cartridge by connecting the connecting element of the dispensing tube to a connecting means of the cartridge.

In this way, it can be ensured that the dispensing tube does not detach from the cartridge when the cement dough is pressed out.

It is furthermore proposed that a rod comprising a plate, serving as parts of the applicator, is driven for pressing the cement components out of the cartridge and into the dispensing tube by way of the applicator, wherein the plate pushes on the dispensing plunger of the storage and mixing system.

Such applicators can be used to manually dispense the cement dough. Moreover, such applicators have a simple composition and are cost-effective.

In one refinement of the method according to the invention, it may be provided that the partition is connected to a cap, and that, in step a), the partition connected to the cap is pulled completely out of the cartridge toward the outside by pulling the cap or a handle of the cap.

Using the cap, the partition can be easily pulled out of the cartridge manually.

Finally, it may also be provided that the applicator can be driven manually, or can be driven by compressed air or electrically.

Manually drivable applicators are preferred according to the invention, since these do not need to be connected to a compressed air source or an energy source, nor do they have to include the same.

The invention is based on the surprising finding that it is possible, by way of a simple pull-out partition, to divide a cylindrical inner chamber of a cartridge into two cavities suitable for storing pasty cement components of a PMMA bone cement. Equally surprisingly, it was found that the time before two pasty cement components react with one another and cure in the inner chamber of the cartridge thus connected, and thus render the storage and mixing system unusable, is sufficient for replacing the cartridge head with a dispensing tube and inserting the storage and mixing system into an applicator, so as to then press out and apply the PMMA bone cement. Furthermore, surprisingly it was found that in this way a narrow cartridge comprising only a single dispensing plunger can be used to move the two cement components forward. The force that is necessary for mixing and driving out the cement components can thus be minimized, so that an applicator to be driven by way of manual force can be used together with the storage and mixing system so as to drive the cement components from the cartridge and mix these with one another.

The invention is based on the idea of using only one cylindrical cartridge, instead of multiple side-by-side cartridges or coaxial cartridges, for the separate storage of the two pasty cement components so as to minimize the flow resistance during dispensation. To avoid two push rods and two plates for driving two dispensing plungers, the cylindrical cartridge is equipped with a partition that can be pulled out axially, which divides the inner chamber of the cartridge bounded by a dispensing plunger and a cartridge head into two cavities, in which the two pasty cement components can be stored separately during storage. By removing the partition, the flow resistance of the pasty cement components to be pressed out is reduced such that it is also possible to use smaller amounts of the PMMA bone cement, and pressing out is also still possible from narrower cartridges comprising inner chambers having smaller inside diameters. The partition is pulled out of the cartridge directly prior to use. This creates a cylindrical cavity, in which the two pasty cement components can make contact with one another for a few seconds until they are mixed in the static mixer, which can be fastened in front of the dispensing opening.

Immediately after the partition has been removed, in a first embodiment the cartridge head is removed, and the dispensing tube containing a static mixer is connected directly to the cartridge by way of a connecting element. Immediately thereafter, the cartridge comprising the connected dispensing tube is connected to a manually actuatable dispensing device, or to a manually actuatable applicator, and the dispensation of the cement components or of the cement dough begins. These steps require a time expenditure of approximately 5 to 10 seconds. After approximately 30 seconds of continuous actuation of the press-out device or of the applicator, the dispensation of the cement dough, which is to say of the mixed pasty two-component PMMA bone cement, having a maximum total volume of the two pasty cement components of 60 ml is completed. Surprisingly, it was found with the present invention that complete separation of the two cement components a few seconds prior to the pressing process and during the early stage of the pressing process can be dispensed with if the cement dough produced from the pasty cement components has a processing time of at least three minutes. As a result, it is possible to use a simple shared cylindrical cartridge having only a low flow resistance.

In a second embodiment, two plugs are removed on the cartridge head after the partition has been removed, and the dispensing tube comprising the static mixer is connected to the cartridge by way of a connecting element.

The invention is furthermore based on the observation that a highly viscous cement dough can be dispensed from cylindrical cartridges through a dispensing tube comprising a static mixer in an acceptable time and with a force expenditure that is acceptable, as it can be applied manually, using commercially available, manually drivable press-out devices or applicators, if the dispensing plunger has a maximum diameter of 25 mm at the end face.

A storage and mixing system according to the invention for pasty two-component polymethyl methacrylate bone cement is composed, for example, of:
a) a tubular cartridge;
b) two guide elements, which are disposed parallel to the longitudinal axis of the cartridge in or on the inside wall of the cartridge;
c) a dispensing plunger that can be axially displaced in the tubular cartridge and comprises a guide element on the upper end face;
d) a partition that is disposed axially in the tubular cartridge and engages in two guide elements in a form-locked manner, which are disposed in or on the inside wall of the cartridge;
e) a cartridge head, which closes one end of the tubular cartridge, wherein the cartridge head has a slot-shaped opening through which the partition exits via the upper face of the cartridge head;
f) a dispensing tube comprising a fastening means for fastening to the cartridge,
g) wherein the partition divides the cavity formed of the cartridge, the dispensing plunger and the cartridge head into two separate cavities, in which a pasty first cement component A and, separately therefrom, a pasty second cement component B are present, and
h) wherein pulling out the partition through the slot-shaped opening of the cartridge head to the outside combines the two cavities to form an inner chamber of the cartridge, in which the pasty first cement component A and the pasty second cement component B make contact with one another.

It may be provided that axial recesses are present on the inner side of the cartridge, serving as guide elements.

In a first embodiment of the exemplary device, a linear recess is present on the upper end face of the dispensing plunger, wherein the ends of the recesses are seated against one another at the two recesses of the cartridge. In this embodiment, axial ribs are provided on the inner side of the cartridge, serving as guide elements. The lateral surface or the outer end face of the dispensing plunger can comprise detent elements, which prevent the dispensing plunger from moving in a direction opposite that of the cartridge head. This is important when the device is sterilized on the outside with ethylene oxide. During the sterilization with ethylene oxide, a vacuum is applied to remove the air from the sterilization chamber. Due to the negative pressure, an undesirable movement of the dispensing plunger in a direction opposite that of the cartridge head may take place as a result of the evaporation of methyl methacrylate in the two cement components A and B.

In a second embodiment of the exemplary device, a rib is disposed on the upper end face of the dispensing plunger, the ends of the rib being seated against the axial ribs of the cartridge.

In one embodiment, the cavities are implemented by two half-moon-shaped cavities, wherein an axially movable first half-moon-shaped loading plunger comprising a detent element on the plunger back is disposed in the first half-moon-shaped cavity, and an axially movable second half-moon-shaped loading plunger comprising a detent element on the plunger back is disposed in the second half-moon-shaped cavity, wherein the dispensing plunger includes a vent hole and two detent elements. In this embodiment, the two half-moon-shaped loading plungers are disposed directly on the cartridge head prior to the cartridge being loaded. When the pasty cement components are pressed in, these displace the half-moon-shaped loading plungers in the direction of the dispensing plunger. Upon contact with the dispensing plunger, these latchingly engage with one another. When the partition is pulled out, negative pressure develops inside the cartridge, whereby the half-moon-shaped loading plungers are pulled forward in the direction of the cartridge head. To prevent these loading plungers from tilting, it is advantageous if these are connected to the dispensing plunger beforehand by way of a latching engagement.

The partition of the device according to the invention is preferably designed as a panel, which comprises at least one peripheral rubber-elastic seal on the narrow side.

This means that, in the first embodiment, the partition is inserted in a form-locked manner into the two recesses of the cartridge and into the recess of the dispensing plunger, wherein the peripheral rubber-elastic seal of the partition is seated in the recesses and thereby separates the two cavities and the pasty cement components contained therein from one another in a manner impervious to liquid.

In a second embodiment, a peripheral recess is formed on the narrow side of the partition, which is flanked by a rubber-elastic seal disposed parallel thereto. In this embodiment, the partition is pushed with a peripheral recess onto the ribs of the cartridge and the rib of the dispensing plunger. The cavities are sealed by the peripheral rubber-elastic seals.

The pasty cement components comprise the highly volatile monomer methyl methacrylate, which can be polymerized by radical polymerization. For storing the cement components, it is thus indispensable for the cartridge, the cartridge head, the partition and the dispensing plunger to be made of plastic materials that represent a good diffusion barrier for methyl methacrylate. It is thus preferred according to the invention for the cartridge, the cartridge head, the partition and the dispensing plunger to be made of plastic material, wherein preferred plastic materials are polyethylene co-vinyl alcohol (EVOH), polybutylene terephthalate (PBT), polyethylene terephthalate (PET), and polymethylmethacrylate-co-acrylonitrile. Additionally, it is also possible to apply diffusion-resistant metal layers, metal oxide or metalloid oxide layers or plastic layers to the parts that do not come in contact with the cement components. In particular, aluminum layers can be used as metal layers. Suitable metalloid oxide layers are in particular silicon dioxide layers.

For the function of the storage and mixing system, it is necessary for the cartridge to comprise a fastening element for a press-out device at one end, and to include at least one external thread and/or one internal thread and/or at least one element of a bayonet catch and/or at least one detent element of a detent closure as a connecting element at the opposite end.

It may be provided that the cartridge head is formed of a rubber-elastic plate and a safety cap made of plastic material, wherein the safety cap blocks the rubber-elastic plate toward the top by way of a protruding rim, and wherein the rubber-elastic plate has a slot-shaped opening, which divides the rubber-elastic plate into two half-moon-shaped or semi-circular surface areas, wherein a passage, which is closed by a plug, is provided in each half-moon-shaped surface area.

Another exemplary embodiment is characterized in that a plastic plate is disposed on or beneath the rubber-elastic plate in the cartridge head, wherein the plastic plate has a slot-shaped opening, which divides the plastic plate into two half-moon-shaped or semi-circular surface areas, wherein a passage, which is closed by plugs, is provided in each half-moon-shaped surface area. Arranging the additional plastic plate results in an improved diffusion barrier with respect to the methyl methacrylate present in the cement components.

According to the invention, a static mixer is disposed in the dispensing tube. All generally known static mixers may be used as the static mixer. An internal thread and/or an external thread and/or elements of a bayonet catch and/or detent elements of a detent closure are attached to the base of the dispensing tube as connecting means. These connecting means can be used to connect the dispensing tube to the cartridge in a mechanically stable manner. This connection must be stable, so that the high pressure that occurs when the pasty cement components are pressed out does not cause the dispensing tube to become detached from the cartridge. Threads are thus particularly advantageous connecting means, and double threads are especially particularly advantageous.

In one embodiment variant, the end face of the cartridge is designed as a cartridge head, comprising at least one slot-shaped opening that divides the end face into two half-moon-shaped or semi-circular surface areas, wherein a passage, which is closed by a plug, is provided in each half-moon-shaped surface area. These passages can have a cylindrical, half-moon-shaped or kidney-shaped design. Corresponding to the geometry of these openings, the plugs also have a cylindrical, half-moon-shaped or kidney-shaped cross-section. It is particularly advantageous if the plugs comprise detent elements on the lower face, so the plugs cannot detach from the passages.

In an advantageous embodiment of the invention, a hollow cap surrounding the cartridge head is disposed over the cartridge head, wherein the upper end of the cap is designed as a handle, and wherein detent elements are disposed at the lower rim of the cap, which connect the cap to the cartridge head in a reversibly detachable manner. The particular advantage of this cap comprising a handle is that the cartridge head is protected against accidental dismounting and that, when the cap is removed, the partition is necessarily pulled along. The cartridge head can only be removed after the cap, together with the partition connected thereto, has been removed.

A method according to the invention for mixing the two pasty cement components of the pasty polymethyl methacrylate bone cement using the storage and mixing system according to the invention is also exemplary, comprising the following steps taking place consecutively:

a) manually pulling the partition completely out of the cartridge head, wherein the first cavity together with the second cavity forms a shared inner chamber of the cartridge in which the pasty cement components make contact with one another;
b) detaching the connecting element connecting the cartridge head to the cartridge, and removing the cartridge head from the cartridge;
c) placing the dispensing tube, which comprises a static mixers, onto the opened cartridge;
d) connecting the dispensing tube to the cartridge by connecting the connecting means of the dispensing tube to the connecting means of the cartridge;
e) connecting the cartridge to a manually actuatable applicator;
f) actuating the applicator, wherein a rod comprising a plate is advanced, pushing against the dispensing plunger;
g) pressing out the two pasty cement components by axially moving the dispensing plunger in the direction of the dispensing tube, wherein the two cement components are mixed by the action of the static mixer in the dispensing tube, forming a homogeneous cement dough; and
h) pressing the homogeneous, mixed cement dough out of the dispensing opening of the dispensing tube to the outside.

The partition connected to the closing cap can be pulled completely out of the cartridge to the outside by pulling the closing cap.

In one variant of the method, an applicator driven by way of compressed air or electric power is used instead of the manually actuatable applicator.

Another exemplary method for mixing the two pasty cement components of the pasty polymethyl methacrylate bone cement is characterized by the following steps taking place consecutively:

a) pulling the partition completely out of the cartridge head, wherein the first cavity together with the second cavity forms a shared inner chamber where the two pasty cement components make contact with one another;
b) removing the plug from the passages of the cartridge head;
c) placing the dispensing tube, which comprises a static mixers, onto the opened cartridge;
d) connecting the dispensing tube to the cartridge by connecting the connecting means of the dispensing tube to the connecting means of the cartridge;
e) connecting the cartridge to a manually actuatable applicator;
f) actuating the applicator, wherein a rod comprising a plate is driven out, pushing against the dispensing plunger;
g) pressing out the two cement components by axially moving the dispensing plunger in the direction of the dispensing tube, wherein the pasty cement components are mixed by the action of the static mixer in the dispensing tube, forming a homogeneous cement dough; and
h) pressing the homogeneous, mixed cement dough out of the dispensing opening of the dispensing tube to the outside by actuating the applicator.

In this exemplary method, the device does not comprise a separate cartridge head. An end face of the cartridge is designed as the cartridge head.

BRIEF DESCRIPTION OF THE DRAWINGS

Exemplary embodiments of the invention will be described hereafter based on eleven schematically illustrated figures, however without thereby limiting the invention. In the drawings.

DETAILED DESCRIPTION OF THE DISCLOSURE

Figure 1:
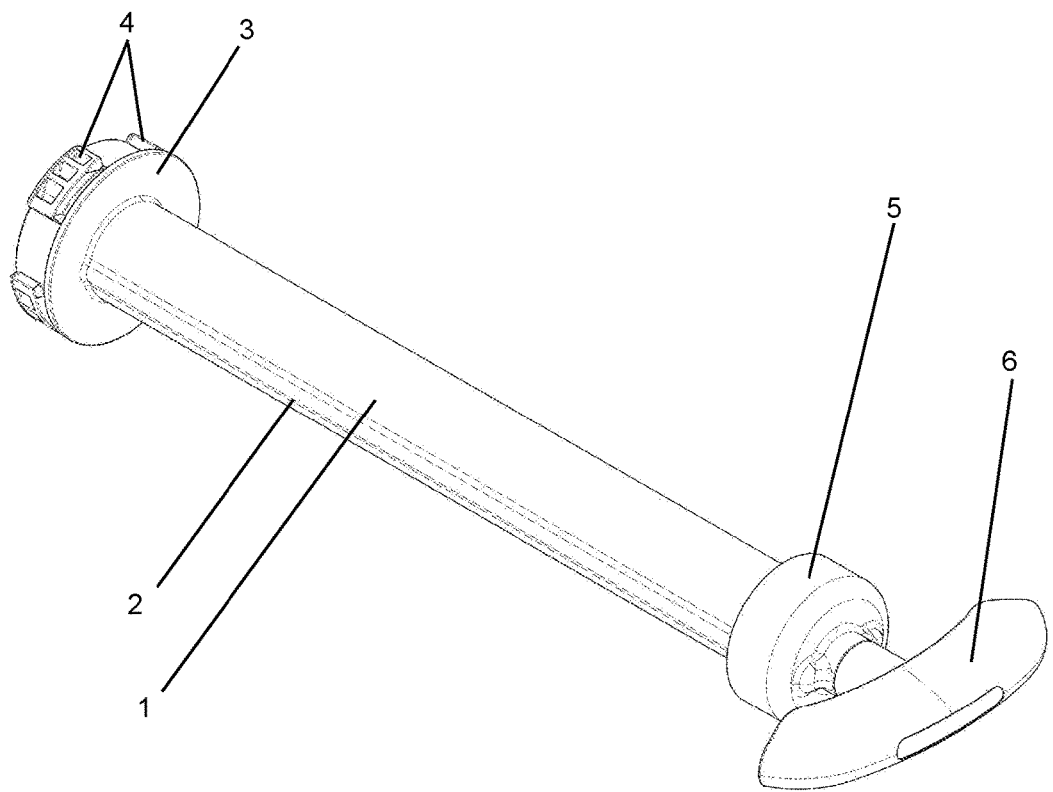
FIG. 1 shows a schematic perspective view of a storage and mixing system according to the invention.

For the sake of simplicity, identical and like components of different embodiments in the figures are in part denoted by the same reference numerals.

FIG. 1 shows a schematic perspective view of a storage and mixing system according to the invention. The simple composition on the outside is apparent from FIG. 1. The storage and mixing system comprises a cylindrical cartridge 1 as a central component, on which an axial groove 2 is provided as a guide element on each of two opposing inner sides. Due to the uniform wall thickness of the cartridge 1, the groove 2 is also apparent from FIG. 1 from the outside as an axial curvature. To be precise, the groove 2 is thus not apparent from FIG. 1, but the material protuberance along the cartridge wall on the back side of the groove 2 is. Nonetheless, the position of the groove 2 was identified in FIG. 1 to clarify the axial position of the groove 2.

On the cartridge bottom or on the bottom side (on the left in FIG. 1), a connector 3 comprising fastening elements 4 is disposed on the cartridge 1. The cartridge 1 can be connected to a dispensing device or an applicator (not shown) by way of the connector 3 and the fastening elements 4. A hollow cap 5, which covers the front side or a cartridge head disposed there beneath (not visible in FIG. 1), is placed onto the opposite front side (on the right in FIG. 1) of the cartridge 1. Moreover, a handle 6, which extends into the inside of the cartridge 1, is disposed on the front side of the cartridge 1. The handle 6 is preferably connected to or latchingly engaged in the cap 5 and can be considered to be part of the cap 5.

The cartridge 1 has an outside diameter of 22 mm, an inside diameter of 20 mm, and a length of approximately 18 cm.

Figure 2:
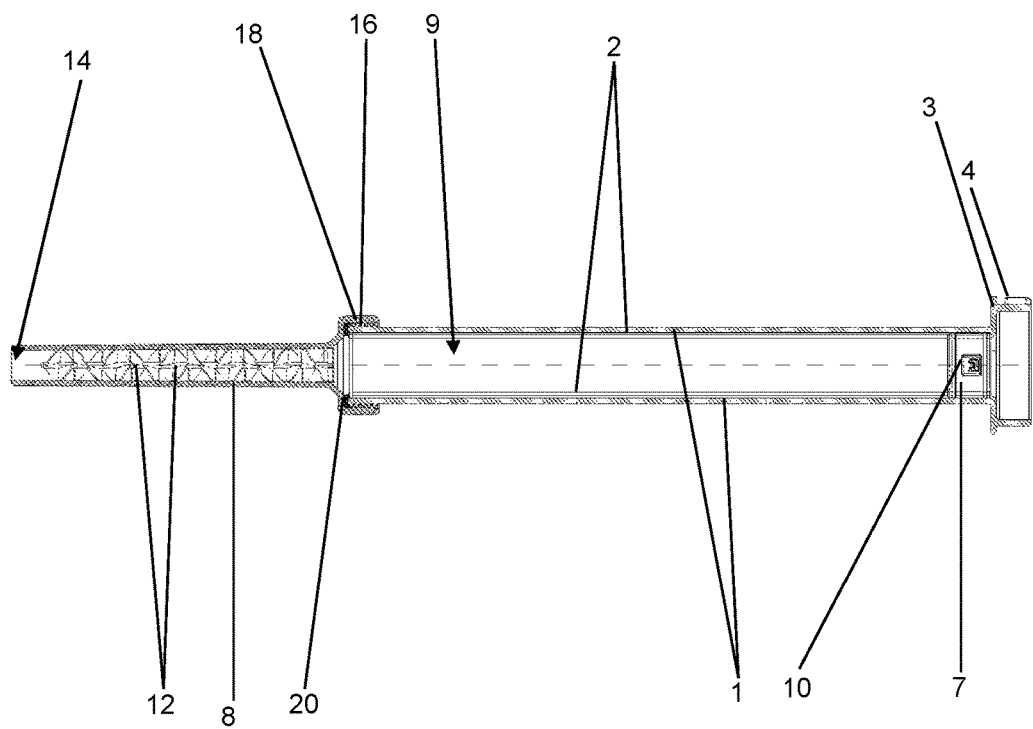
FIG. 2 shows a schematic cross-sectional view through the storage and mixing system according to the invention of FIG. 1 immediately prior to the application of the PMMA bone cement, in which the cap and the handle were removed, and the cartridge head has been replaced with a dispensing tube.
Figure 3:
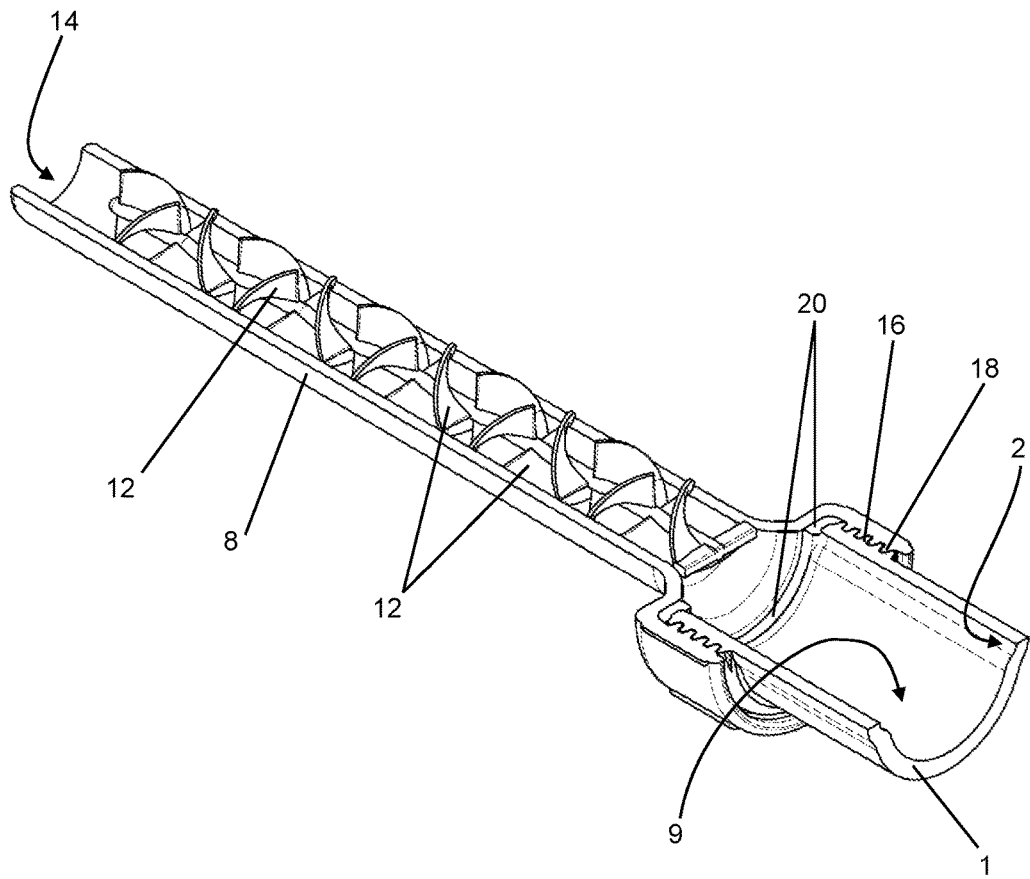
FIG. 3 shows a schematic perspective cross-sectional view of the front portion (on the left in FIG. 2) of the storage and mixing system according to the invention of FIG. 2.

FIG. 2 shows a schematic cross-sectional view through the storage and mixing system according to the invention of FIG. 1 immediately prior to the application of the PMMA bone cement, in which the cap 5 and the handle 6 were removed, and the cartridge head has been replaced with a dispensing tube 8. FIG. 3 shows a schematic perspective partial cross-sectional view of the front portion (on the left in FIG. 2) of the storage and mixing system according to the invention of FIG. 2.

On the bottom, an axially movable dispensing plunger 7 is disposed in the inner chamber 9 of the cartridge 1. The dispensing plunger 7 is connected to two releasable detent elements 10 having suitable mating detent elements (in the form of two depressions) in the inside wall of the cartridge 1. The dispensing plunger 7 can be driven by way of pressure from the back side of the cartridge 1 (on the right in FIG. 2) in the direction of the front side of the cartridge 1 (on the left in FIG. 2), which is to say in the direction of the dispensing tube 8. The detent elements 10 can be readily released by the application of pressure to the bottom of the dispensing plunger 7 and are primarily used to prevent the dispensing plunger 7 from being pressed out of the cartridge 1 at the bottom when the inner chamber 9 of the cartridge 1 is being loaded with cement components, or from being pressed beyond the position defined by the mating detent elements in the inside wall of the cartridge 1 in the direction of the cartridge bottom (on the right in FIG. 2).

The advancement of the dispensing plunger 7 is generated by way of an applicator (not shown), which is connected to the connector 3 and by way of which a rod comprising a plate thereon can be advanced manually in the direction of the dispensing tube 8. The plate then pushes against the dispensing plunger 7, thereby releasing the detent elements 10 and driving the dispensing plunger 7 forward in the direction of the dispensing tube 8. The dispensing plunger 7 is hermetically sealed with respect to the inside walls of the cartridge 1. The dispensing plunger 7 thus also replicates the contour of the groove 2 of the cartridge 1. In this way, the content of the inner chamber 9 of the cartridge 1, which is to say two pasty cement components present in the inner chamber 9, can be driven forward out through the dispensing tube 8.

The dispensing tube 8 includes a static mixer 12, which thoroughly mixes the two cement components with one another before the cement dough thus mixed exits via a dispensing opening 14 at the front tip of the dispensing tube 8 and can be applied. The dispensing tube 8 can be even longer than the dispensing tube 8 shown in FIG. 2 (see also FIG. 11 in this regard) so as to make regions that are difficult to access easier to reach, as may be helpful during hip surgeries, for example. FIG. 3 shows all parts, except for the static mixer 12, in a sectional view, while the static mixer 12 is shown in a perspective illustration and protrudes from the cutting plane. The section according to FIG. 3 is parallel to the section according to FIG. 2. Both sections are located in the plane of the two grooves 2 and the axis of the storage and mixing system. The axis of the storage and mixing system is identified by a dash-dotted line in FIG. 2. The two grooves 2 are thus located laterally reversed opposite one another and parallel to the axis of the storage and mixing system.

An external thread 16, onto which an internal thread 18 of the dispensing tube 8 is screwed, whereby the dispensing tube 8 is fastened to the front side of the cartridge 1, is disposed on the front side of the cartridge 1. So as to seal the dispensing tube 8 with respect to the cartridge 1, a peripheral seal 20 is disposed between the front stop of the cartridge 1 and the suitable mating piece of the dispensing tube 8. The seal 20 prevents cement dough or the cement components from being able to be pressed to the outside between the dispensing tube 8 and the cartridge 1 and thus contaminate the surrounding area.

The dispensing tube 8 is approximately 10 cm long (however, it may also be 20 cm long or even slightly longer) and has an inside diameter of approximately 12 mm.

Figure 4:
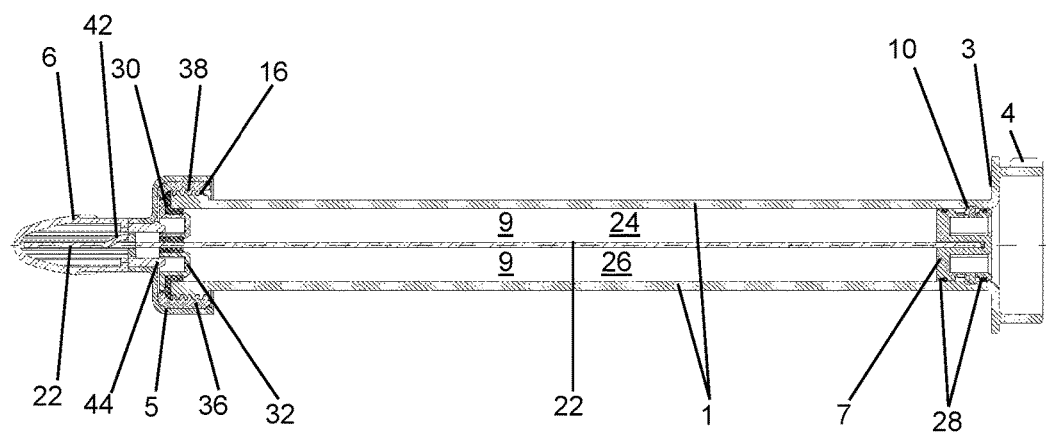
FIG. 4 shows a schematic cross-sectional view through the storage and mixing system according to the invention of FIG. 1.
Figure 5:
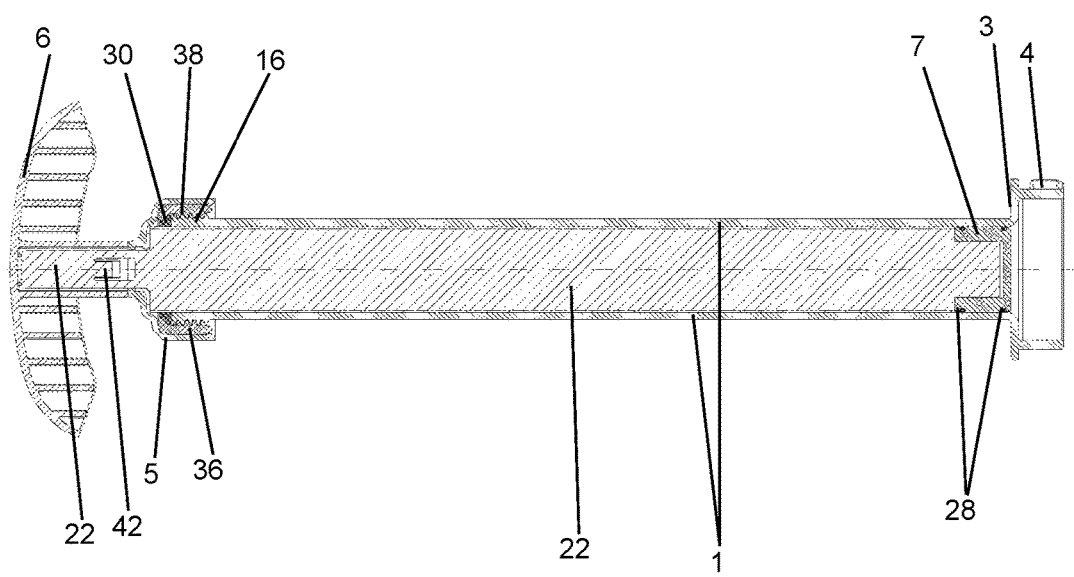
FIG. 5 shows a schematic cross-sectional view through the storage and mixing system according to the invention of FIG. 1 in a section perpendicular to the cross-section shown in FIG. 4.

FIG. 4 shows a schematic cross-sectional view through the storage and mixing system according to the invention of FIG. 1, which is to say in the starting condition. The section through the cartridge 1 according to FIG. 4 is perpendicular to the section through the cartridge 1 according to FIG. 2, wherein in both sections the axis of the storage and mixing system is disposed in the cutting plane. FIG. 5 shows a schematic cross-sectional view through the storage and mixing system according to the invention of FIG. 1 in a section perpendicular to the cross-section shown in FIG. 4, which is to say parallel to the section of the cartridge 1 according to FIG. 2. The axis of the storage and mixing system is also identified by a dash-dotted line in FIG. 4 and in FIG. 5.

A partition 22 is an essential and central component of the storage and mixing system according to the invention, which extends along the axis of the storage and mixing system and can be pulled axially out of the inner chamber 9 of the cartridge 1. The partition 22 rests laterally against the inside wall of the cartridge 1 in the two grooves 2, which hold and position the partition 22 in the inner chamber 9 of the cartridge 1. The partition 22 is hermetically sealed with respect to the inside wall of the cartridge 1 across the full length at the grooves 2 in a fluid-tight manner, thereby separating the inner chamber 9 of the cartridge 1 into two equally sized cavities 24, 26 that are separated from one another in a fluid-tight manner. The first pasty cement component is present in the first cavity 24, and the second pasty component is present in the second cavity 26.

The partition 22 is held in a suitable slot in the dispensing plunger 7 or inserted into the slot, wherein the slot in the dispensing plunger 7 connects flush with the grooves 2, or is aligned with the grooves 2, and positions, holds and seals the partition 22. The dispensing plunger 7 is sealed with respect to the inside walls of the cartridge 1 by way of two peripheral seals 28, so that the cement components cannot leak between the cartridge 1 and the dispensing plunger 7.

A rubber-elastic plate 30, serving as the cartridge head 30, is fastened to the front side of the cartridge 1 (on the left in FIGS. 4 and 5). Two passages having a cross-section in the shape of the segment of a circle, or having a semi-circular or half-moon-shaped cross-section, are provided in the cartridge head 30. Two plugs 32 having a suitable cross-section are inserted into these passages so that the passages, and consequently the cavities 24, 26, are tightly closed. The cavities 24, 26, and consequently the two cement components, would be accessible from the outside through the passages if these were not closed by way of the plugs 32.

Figure 6:
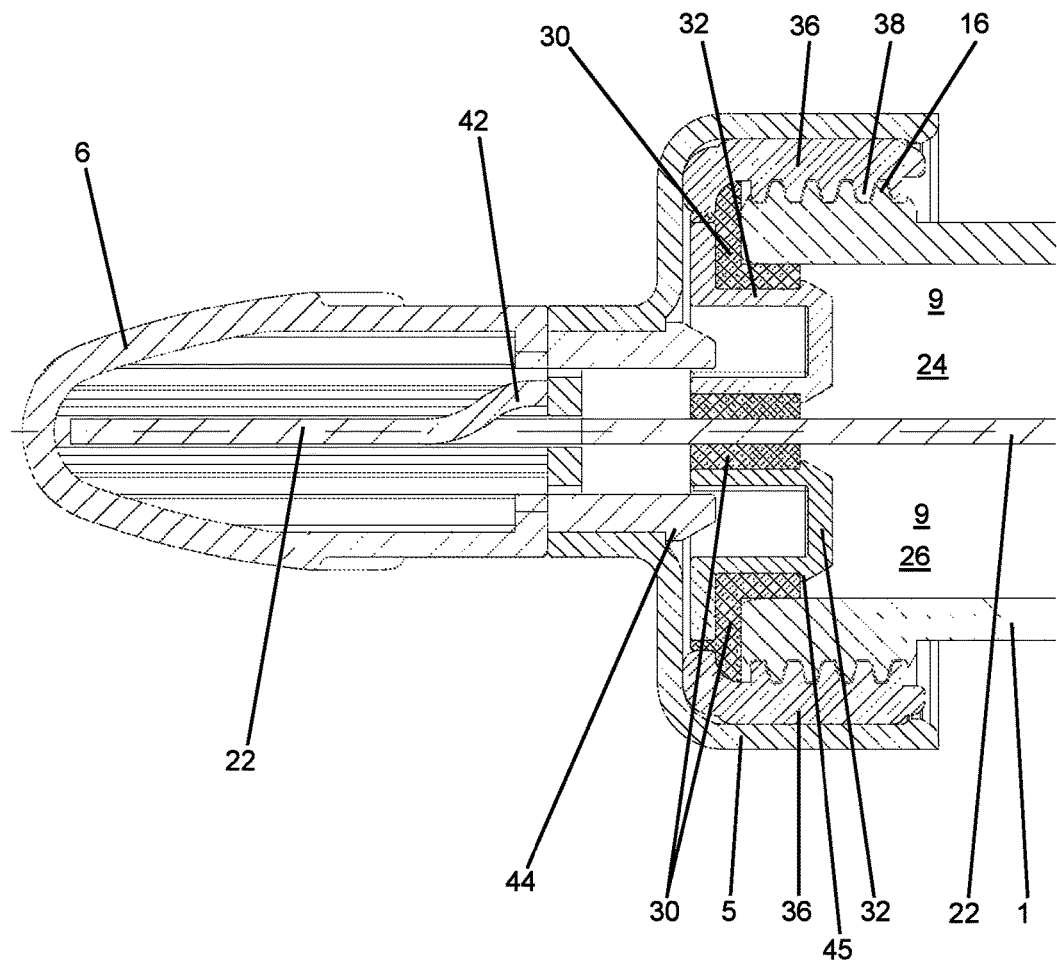
FIG. 6 shows an enlarged schematic cross-sectional view of the front side of the storage and mixing system according to the illustration of FIG. 4.
Figure 7:
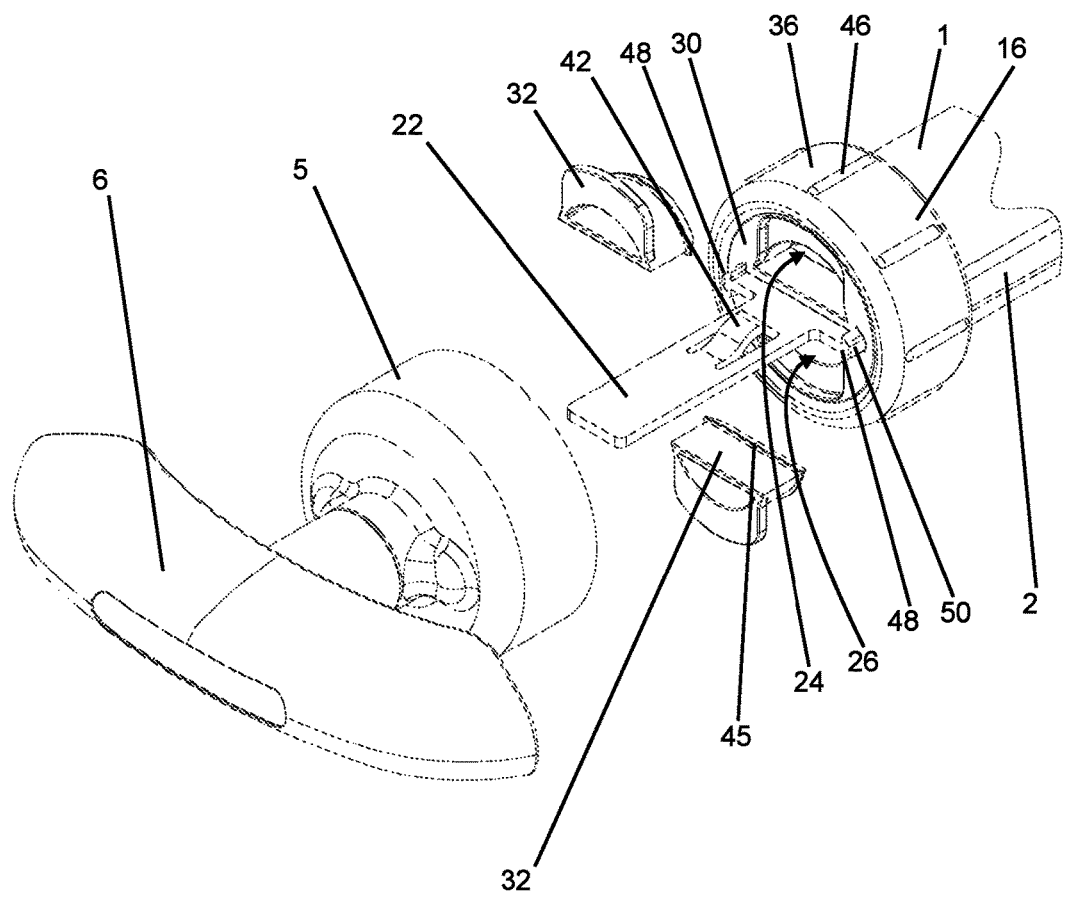
FIG. 7 shows an enlarged schematic perspective view of the front side of the storage and mixing system of FIGS. 1, 4, 5 and 6 in an exploded view.

For the sake of improved clarity of the composition of the storage and mixing system in the region of the front side thereof, enlarged illustrations are shown in FIGS. 6 and 7. FIG. 6 shows an enlarged detail of the front of the storage and mixing system according to the schematic cross-sectional view of FIG. 4, and FIG. 7 shows an enlarged schematic perspective view of the front side of the storage and mixing system according to FIGS. 1, 4, 5 and 6 in an exploded illustration.

The cartridge head 30 comprising the plugs 32 in the passages of the cartridge head 30 is held by a union nut 36 comprising an internal thread 38, which is screwed onto the external thread 16 of the cartridge 1, onto which the dispensing tube 8 is also screwed when the cartridge head 30 or the entire assembly of the front side of the cartridge 1 has been removed. In the present example, the union nut 36, together with the rubber-elastic plate 30, is considered the cartridge head 30, 36. The plugs 32 can also be considered to be part of the cartridge head 30, 36. As a result of this composition, the cartridge head 30, 36 or the union nut 36 and the rubber-elastic plate 30, together with the plugs 32 in the passages of the rubber-elastic plate 30, hermetically seals the front side of the storage and mixing system and the two cavities 24, 26.

A slot-shaped opening is provided in the cartridge head 30, or more precisely in the rubber-elastic plate 30, through which the partition 22 extends from the inner chamber 9 of the cartridge 1 to the outside. For this purpose, the partition 22 is seated against the slot-shaped opening, so as to be positioned and sealingly mounted by the slot-shaped opening, and so as to scrape material of the two pasty cement components adhering to the partition 22 off on the slot-shaped opening of the rubber-elastic plate 30 when the partition 22 is being pulled out of the cartridge 1, or out of the inner chamber 9 of the cartridge 1, through the slot-shaped opening. The partition 22 forms a rectangular panel in the inner chamber 9 of the cartridge 1 and in the slot-shaped opening of the rubber-elastic plate 30.

A detent tongue 42 is provided in the region of the partition 22 located outside the cartridge 1 or, as seen from the inner chamber 9, on the other side of the cartridge head 30. This detent tongue 42 can be used to connect the partition 22 to the handle 6. Moreover, catches 44, which engage in the cap 5, are provided on the handle 6. Catches 45, which latchingly engage with the rubber-elastic plate 30, are likewise provided on the plugs 32.

According to the invention, the production of a storage and mixing system according to the invention can take place as follows: The cartridge 1, comprising the connector 3 thereon, is provided. The dispensing plunger 7 is inserted into the bottom of the cartridge 1 until the two detent elements 10 engage in the depressions in the inside wall of the cartridge 1. The rubber-elastic plate 30 is fastened by way of the union nut 36 onto the front side of the cartridge 1, or is screwed onto the external thread 16 of the cartridge 1. The partition 22 is inserted through the slot-shaped opening in the rubber-elastic plate 30 into the inner chamber 9 of the cartridge 1. The edges 48 of the partition 22 are guided in the grooves 2 in the inside walls of the cartridge 1. For this purpose, the cartridge 1 can be compressed perpendicularly to the axis and perpendicularly to the grooves 2 so as to increase the distance between the grooves 2 and facilitate the insertion of the partition 22. Finally, the partition 22 is pushed into the slot in the dispensing plunger 7, whereby the inner chamber 9 of the cartridge 1 is divided into two separate cavities 24, 26.

Through the passages in the rubber-elastic plate 30, which are still open, the cavities 24, 26 are loaded with the two pasty cement components separately from one another, and subsequently the cavities 24, 26 are closed to the outside by inserting the plugs 32. To this end, the plugs 32 are inserted into the passages until the catches 45 of the plugs 32 latchingly engage with the rubber-elastic plate 30 and can no longer readily exit the passages.

Thereafter, the cap 5 is placed on, and then the handle 6 is placed onto the cap 5, wherein the detent tongue 42 of the partition 22 latching engages with the handle 6, and the catch 44 of the handle 6 latchingly engages with the cap 5. The storage and mixing system is thus completely assembled and can be used for storage.

Immediately prior to use of the storage and mixing system, the partition 22 is pulled out through the slot-shaped opening of the rubber-elastic plate 30 using the handle 6. The two cement components can now make contact with one another in the inner chamber 9 of the cartridge 1. The union nut 36 is unscrewed and removed together with the rubber-elastic plate 30 and the plugs 32. Instead, the dispensing tube 8 is screwed onto the cartridge 1, and this assembly is inserted into an applicator (not shown). Using the applicator, the cement components are pressed out of the inner chamber 9, which is then shared, of the cartridge 1 and into the dispensing tube 8 with the aid of the dispensing plunger 7, where these are mixed by way of the static mixer 12, and the fully mixed cement dough is applied via the dispensing opening 14.

Ribs 46 are provided on the union nut 35, which create a distance between the union nut 35 and the cap 5, which has a smooth cylindrical inside surface. This allows a sterilizing gas, such as ethylene oxide, to penetrate between the cap 5 and the union nut 35, and the storage and mixing system can be sterilized more easily, or more completely, for the use in the operating room area.

The edges 48 of the partition 22 are widened and have a mushroom-shaped cross-section so as to achieve a better sealing action across a large abutment surface in the matching grooves 2 of the inside walls of the cartridge 1. Moreover, rubber-elastic seals 50 are provided along the edges 48, which can be improve the sealing action of the partition 22 in the cylinder 1, whereby longer-term storage of the cement components in the cavities 24, 26 is made possible.

Figure 8:
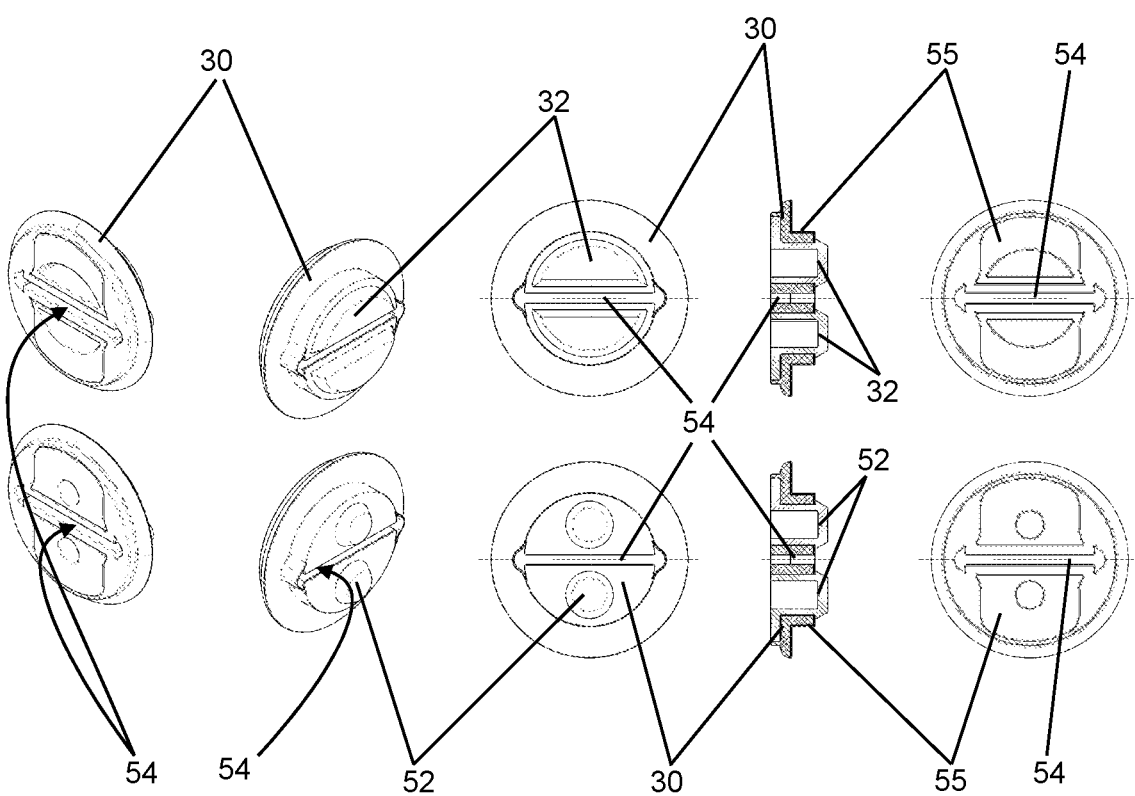
FIG. 8 shows multiple schematic illustrations of two different plates for assembling cartridge heads of storage and mixing systems according to the invention.

FIG. 8 shows several schematic illustrations of two different rubber-elastic plates 30 (first variant at the top of FIG. 8 and second variant at the bottom of FIG. 8), each having two differently shaped passages. The variants are illustrated in perspective views and in a respective cross-sectional view. A plug 32, 52 is inserted and latching engaged in each of the two passages. The rubber-elastic plates 30 and the plugs 32, 52 are suitable for assembling cartridge heads of storage and mixing systems according to the invention. The rubber-elastic plates 30 differ with respect to the shapes of the passages thereof and the shapes of the plugs 32, 52 that close these passages. In the first variant (top of FIG. 8), the passages and the plugs 32 have a semi-circular or half-moon-shaped cross-section. In the second variant (bottom of FIG. 8), the passages and the plugs 52 have a circular cross-section. In the first variant, the free cross-section for loading the two cement components is larger than in the second variant. In the second variant, the geometry is adapted to loading pipes or syringes (not shown), by way of which the cavities 24, 26 are loaded with the cement components, so that the loading pipes or syringes are hermetically sealed with respect to the passages. The plugs 32, 52 can also be removed in order to dispense the cement components from the inner chamber 9 of the cartridge 1 again, if the entire cartridge head 30, 36 is not supposed to be removed.

In the two shown variants, a slot-shaped opening 54, through which the partition 22 is guided and through which the partition 22 can be pulled out of the inner chamber 9 of the cartridge 1, is provided in the rubber-elastic plate 30 between the respective passages. In the two variants shown in FIG. 8, flat plastic disks 55 are placed onto the rubber-elastic plates 30 on the sides facing the inner chamber 9 of the cartridge 1. These plastic disks 55 are used to stabilize the shape of the rubber-elastic plates 30 on the one hand, and to improve the chemical stability of the receptacle or of the cavities 24, 26 for the cement components on the other hand.

Figure 9:
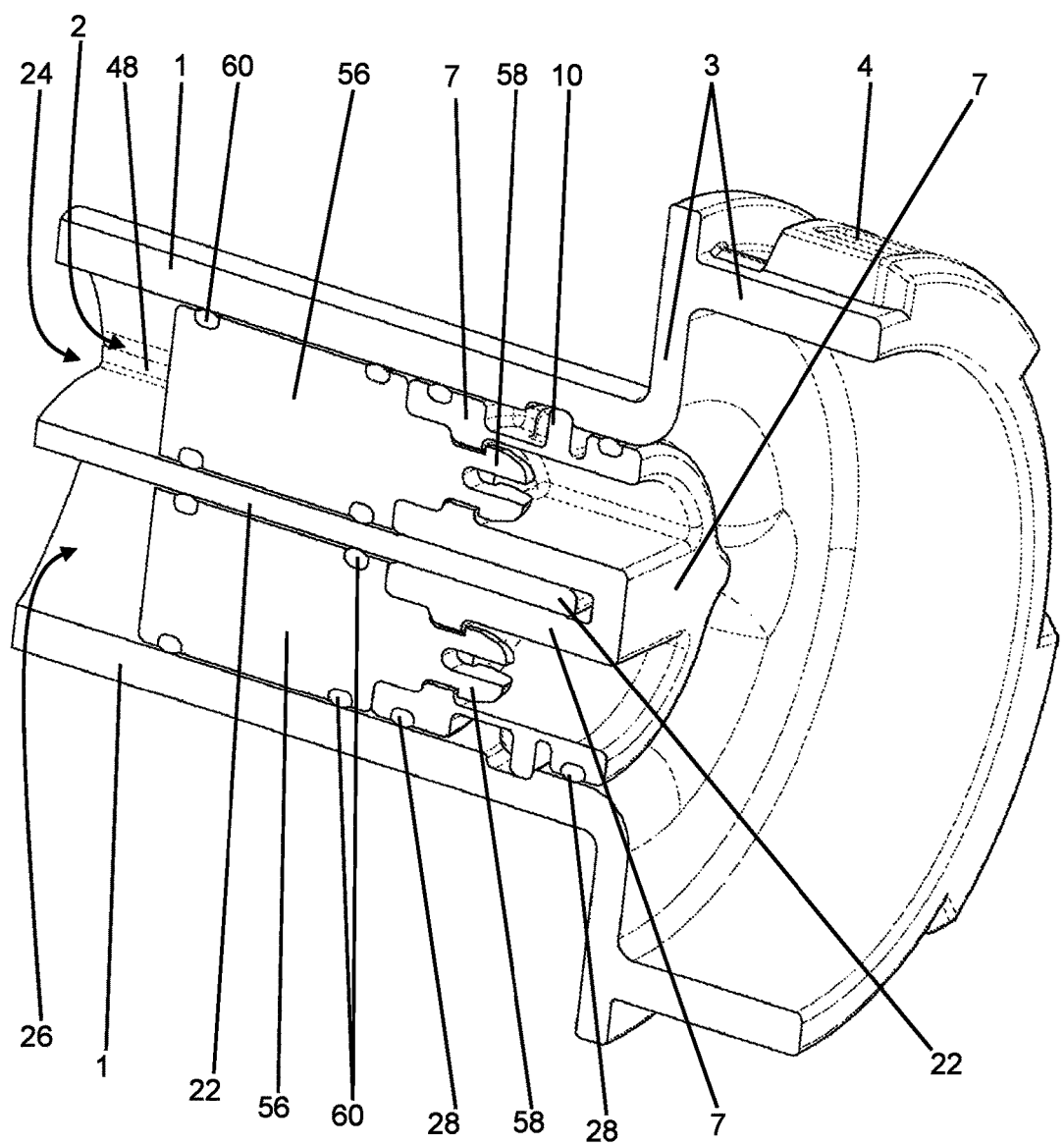
FIG. 9 shows an enlarged schematic perspective cross-sectional view of the cartridge bottom of a storage and mixing system according to the invention.
Figure 10:
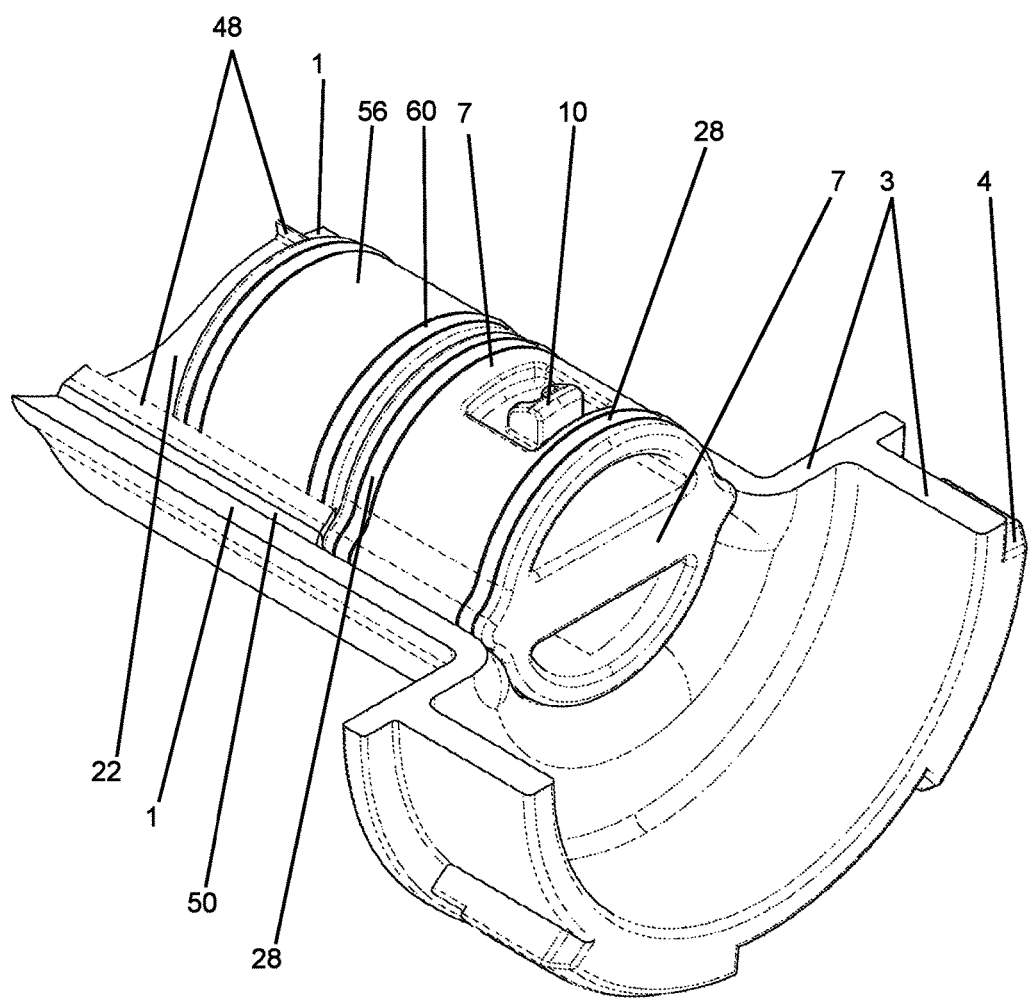
FIG. 10 shows an enlarged schematic perspective partial cross-sectional view of the cartridge bottom of the storage and mixing system according to the invention of FIG. 9.

FIG. 9 shows an enlarged schematic perspective cross-sectional view of the cartridge bottom of a further alternative storage and mixing system according to the invention, in which the loading of the cement components is facilitated. In principle, the storage and mixing system is composed in the same manner as the storage and mixing systems illustrated in FIGS. 1 to 8, or with the parts shown there. FIG. 10 shows an enlarged schematic perspective partial cross-sectional view of the cartridge bottom of the storage and mixing system according to the invention of FIG. 9.

In this variant embodiment of the present invention, a loading plunger 56 is disposed in each of the cavities 24, 26. Initially, not as shown in FIG. 9, the loading plungers 56 are seated against the rubber-elastic plate 30 (not visible in FIG. 9) behind the two passages in the cavities 24, 26. When the cement components are loaded, the two loading plungers 56 are pushed by the cement components in the direction of the dispensing plunger 7. This prevents having to guide a loading tube through the passages in the rubber-elastic plate 30 to the dispensing plunger 7 so as to load the cement components, without creating air pockets in the cavities 24, 26. The shown storage and mixing system can thus be used to achieve simplified loading of the cavities 24, 26, without trapping air in the pasty cement components within the cavities 24, 26 when loading the cement components.

Detent elements 58 are disposed in the loading plungers 56, the detent elements facing in the direction of the cartridge bottom, which is to say in the direction of the dispensing plunger 7, and latchingly engaging with openings, serving as mating detent means, in the dispensing plunger 7 when the loading plungers 56 are pushed against the dispensing plunger 7 by way of the added cement components. The two openings in the dispensing plunger 7 are continuous to allow air between the loading plunger 56 and the dispensing plunger 7 to escape through the two openings. The loading plungers 56 close off the cavities 24, 26 and, for this purpose, are each sealed by two peripheral seals 60 with respect to the inside wall of the cartridge 1 and with respect to the partition 22, which laterally bound the cavities 24, 26.

It is easily apparent from FIG. 9 that the dispensing plunger 7 also replicates the shape of the groove 2, at least on the bottom. This is also the case in the other variants. In the variant according to FIG. 9, this is necessary since the loading plungers 56 cannot engage in the groove 2, and it is not desirable for the cement components to be able exit the storage and mixing at the bottom through the grooves 2 when the cement components are pressed out by way of the dispensing plunger 7.

Instead of the detent elements 10 comprising the depressions as mating detents in the inside walls of the cartridge 1, the groove 2 can also be closed on the bottom, or a ring can be provided on the inside wall of the cartridge 1, preventing further movement of the dispensing plunger 7 through the cartridge bottom. The dispensing plunger 7 then has to be pushed from the front side of the cartridge 1 into the inner chamber 9 of the cartridge 1. This embodiment can be implemented for all variants according to the invention, but is not illustrated in any of the figures.

Figure 11:
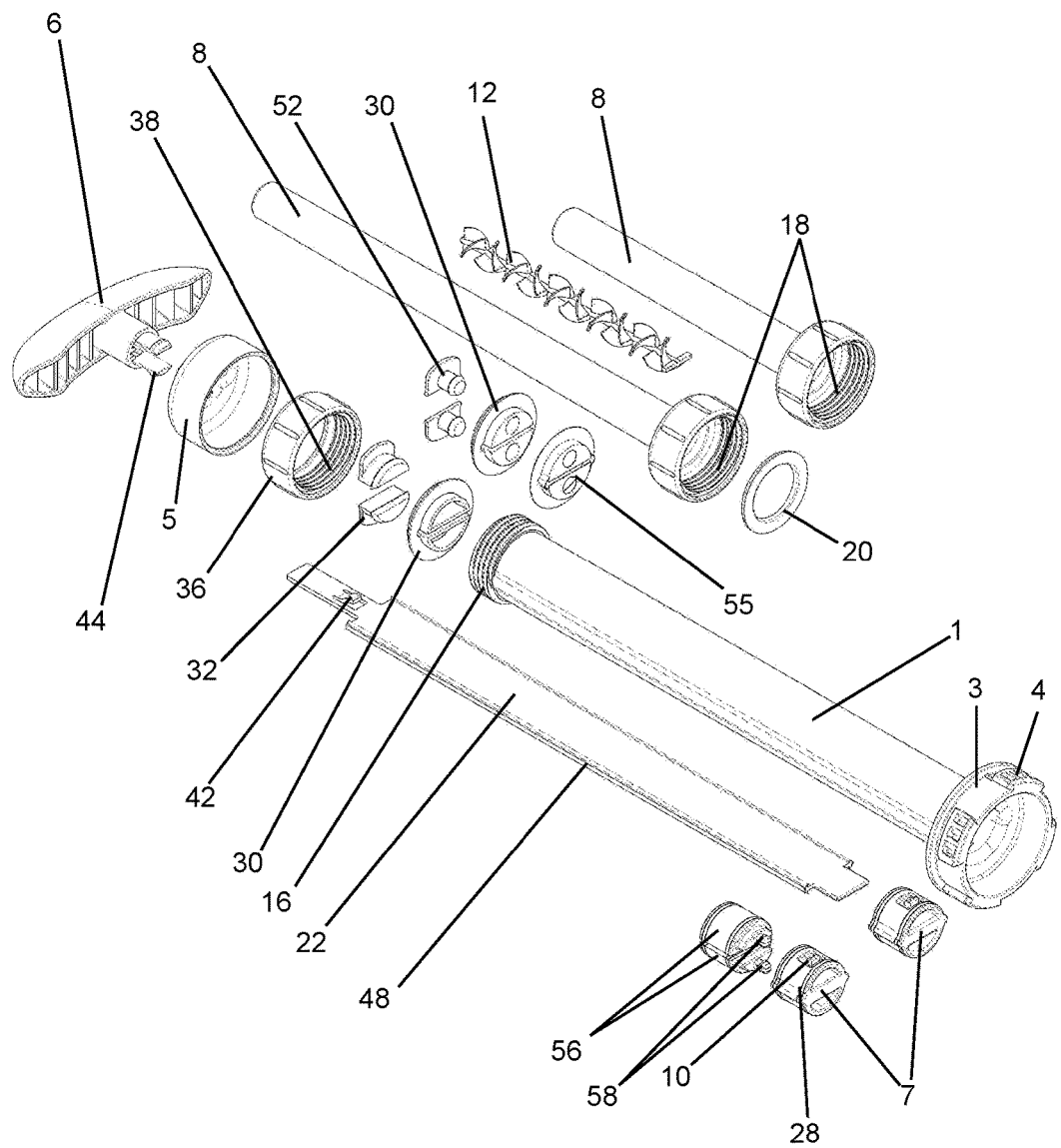
FIG. 11 shows a schematic perspective exploded view, in part with different and alternative parts of storage and mixing system according to the invention.

FIG. 11 shows a schematic perspective exploded view, in part with different and alternative parts for storage and mixing systems according to the invention. The composition of the storage and mixing systems is analogous to the above-described storage and mixing systems.

FIG. 11 shows, for example, two differently long dispensing tubes 8, which can both be screwed with the internal threads 18 thereof onto the external thread 16 of the cartridge 1. The longer dispensing tube 8 can be used to apply the cement dough to regions that are difficult to access. The static mixer 12 and the seal 20 can be used with both dispensing tubes 8.

Likewise, the two alternative variants of the rubber-elastic plates 30 having differently shaped passages are shown, which can be closed by way of the plugs 32, 52. The plastic disk 55 can also (but does not have to) be used with the rubber-elastic plate 30 comprising the passages having the circular cross-section.

The assembly of the tubular cartridge 1 comprising the connector 3, the fastening elements 4, the two grooves 2, and the external thread 16 has the same shape in all variants. It would also be conceivable, of course, to provide only one groove or more than two grooves. Theoretically, the grooves 2 could be implemented helically in the manner of an internal thread in or on the inside walls of the cartridge 1.

The partition 22 would then have to be unscrewed, and the dispensing plunger 7 would also have to rotate during advancement, which would make the implementation of the storage and mixing system more difficult. Instead of the grooves 2, ribs or other elevations could also be provided, which are disposed on the inside wall of the cartridge 1 and in which the partition 22 is held and sealed.

The partition 22 is identical in all shown embodiments. However, it would also be possible to configure the edge 48 in a different or another manner and to increase and/or decrease the abutment surface of the edge 48 against the groove 2 and/or the inside wall of the cartridge 1.

Both the union nut 36 and the dispensing tube 8 can be screwed onto the external thread 16 of the cartridge 1. Variants in which the rubber-elastic plate 30 is fixedly connected to the cartridge 1, or not designed in a rubber-elastic manner and/or in one piece with the cartridge 1, are also conceivable. In this way, no union nut 36 is required, and the dispensing tube 8 can simply be screwed onto the cartridge 1 after the plugs 32, 52 have been removed. The cement components can then simply be pressed through the passages into the dispensing tube 8, where they are mixed by way of the static mixer 12 to yield the desired cement dough.

FIG. 11 also shows the two variants with and without the loading plunger 56. In the variant without the loading plunger 56, the dispensing plunger 7 must be closed, of course, while in the variant with the loading plunger 56, the dispensing plunger 7 has continuous openings for conducting air.

In all variants, the cartridge 1 and the connector 3 are preferably designed in one piece with one another and are preferably made of plastic material. With the exception of the seals 20, 28, 50, 60 and the rubber-elastic plate 30, all parts of the storage and mixing systems can be made of plastic material by way of injection molding. The seals 20, 28, 50, 60 and the rubber-elastic plate 30 are preferably made of rubber. Theoretically, the other parts of the storage and mixing system can also be made of metal materials. Preferred cement components are pasty starting components of a PMMA bone cement. However, theoretically, it is also possible to store and mix other cements, such as dental cements, two-component adhesives or other two-component systems that are mixed from pasty starting components, using a storage and mixing system according to the invention.

The characteristics of the invention disclosed in the above description, as well as in the claims, figures and exemplary embodiments may be essential for the implementation of the invention in its various embodiments either alone or in any arbitrary combination with each other.

LIST OF REFERENCE NUMERALS 1 cartridge
2 groove/guide element
3 connector
4 fastening element
5 cap
6 handle
7 dispensing plunger
8 dispensing tube
9 inner chamber
10 releasable detent element
12 static mixer
14 dispensing opening
16 external thread
18 internal thread
20 seal
22 partition
24 first cavity
26 second cavity
28 seal
30 plate/cartridge head
32 plunger
36 union nut/cartridge head
38 internal thread
42 detent tongue
44 catch
45 catch
46 rib
48 edge
50 seal
52 plunger
54 slot-shaped opening
55 plastic disk
56 loading plunger
58 detent element
60 seal

We claim:

1. A storage and mixing system for pasty two-component bone cements, the system comprising:
a tubular cartridge having a cylindrical inner chamber;
a dispensing plunger that is axially displaceable in the inner chamber of the tubular cartridge;
a partition panel disposed axially in the tubular cartridge; and
a cartridge head closing one end of the tubular cartridge,
wherein the cartridge head has a slot-shaped opening and the partition panel protrudes from the inner chamber of the cartridge through the slot-shaped opening of the cartridge head,
wherein the partition panel divides the cylindrical inner chamber of the cartridge bounded by the dispensing plunger and the cartridge head into two cavities that are spatially separated from one another,
wherein the partition panel separates the cylindrical inner chamber of the cartridge in a manner impervious to liquid, and the two cavities are separated from one another in a manner impervious to liquid,
wherein a first pasty cement component is present in a first cavity and a second pasty cement component is present in a second cavity, and
wherein the partition panel is removable through the slot-shaped opening of the cartridge head such that the first and second cavities are connected to one another after the partition panel is removed.

2. The storage and mixing system according to claim 1, wherein the dispensing plunger is disposed at the end opposite the cartridge head in the inner chamber of the cartridge.

3. The storage and mixing system according to claim 1, further comprising: a dispensing tube on which a fastening means for fastening to the cartridge is provided, wherein the dispensing tube is to be fastened to the cartridge for replacing the cartridge head.

4. The storage and mixing system according to claim 3, wherein a ratio of the diameter of the inner chamber of the cartridge to an inside diameter of the dispensing tube is smaller than 5 to 2.

5. The storage and mixing system according to claim 1, wherein the diameter of the inner chamber of the cartridge is smaller than or equal to 25 mm.

6. The storage and mixing system according to claim 1, wherein the slot-shaped opening is shaped to match the cross-section of the partition panel.

7. The storage and mixing system according to claim 1, wherein the first pasty cement component and the second pasty cement component are in contact with one another after removal of the partition panel.

8. The storage and mixing system according to claim 1, further comprising: at least two guide elements disposed parallel to the longitudinal axis of the cartridge in or on the inside wall of the cartridge, wherein the partition panel engages in the at least two guide elements in a form-locked manner and/or the dispensing plunger comprises a guide element, into which the partition panel is pushed or inserted on the end face delimiting the inner chamber.

9. The storage and mixing system according to claim 8, further comprising: axial recesses provided on the inner side of the cartridge, serving as guide elements, and/or a linear recess provided on the side of the dispensing plunger facing the cartridge head, serving as a guide element, wherein the ends of the linear recesses are aligned with one another at the axial recesses of the cartridge.

10. The storage and mixing system according to claim 8, further comprising: axial ribs provided on the inner side of the cartridge, serving as guide elements, and/or a rib provided on the side of the dispensing plunger facing the cartridge head, wherein the ends of the rib on the dispensing plunger are aligned with one another at the axial ribs of the cartridge.

11. The storage and mixing system according to claim 1, wherein an axial movement of the dispensing plunger in the direction of the cartridge head is blockable by the partition panel if the partition panel spatially divides the inner chamber of the cartridge into the two cavities.

12. The storage and mixing system according claim 1, further comprising:
two passages provided in the cartridge head, that connect the two cavities to the surrounding area of the storage and mixing system, wherein a plug is disposed in each of the passages, wherein the plugs comprise a detent element on the side of the plug facing the inner chamber of the cartridge.

13. The storage and mixing system according to claim 1, wherein the partition panel, on the edge to the connection to the inside wall of the cartridge, comprises at least one peripheral rubber-elastic seal and/or has a widening to achieve sealing with the inside wall of the cartridge across a larger surface area.

14. The storage and mixing system according to claim 1, further comprising:
a loading plunger disposed in each of the cavities, the loading plungers being axially movable in the cavities, wherein the loading plungers are connectable to the dispensing plunger by two mating detent means and at least one vent hole provided in the dispensing plunger, through which air trapped between the loading plunger and the dispensing plunger can escape from the cavities.

15. The storage and mixing system according to claim 1, wherein the cartridge, the cartridge head, the partition panel and the dispensing plunger are made of plastic material selected from polyethylene co-vinyl alcohol (EVOH), polybutylene terephthalate (PBT), polyethylene terephthalate (PET), and polymethylmethacrylate-co-acrylonitrile.

16. The storage and mixing system according to claim 1, wherein the cartridge head is composed with a rubber-elastic plate and a hollow cap, wherein the hollow cap blocks a movement of the rubber-elastic plate away from the cartridge via a protruding rim, and wherein the slot-shaped opening extends through the rubber-elastic plate and divides the rubber-elastic plate into two areas, wherein a passage, which is closed by a plug, is provided in each of the two areas.

17. The storage and mixing system according to claim 1, further comprising: a hollow cap provided as a connecting element for connecting the cartridge head to the cartridge, wherein the hollow cap comprises an internal thread or an external thread or a bayonet catch or detent elements.

18. The storage and mixing system according to claim 1, wherein the partition panel, in the region located outside the inner chamber and outside the cartridge head, comprises at least one fastening means for a pulling device for removing the partition panel from the cartridge.

19. The storage and mixing system according to claim 1, further comprising: a cap disposed on the cartridge head, wherein an upper end of the cap is designed as a handle, and wherein a connecting element is, or detent elements are, disposed at a lower rim of the cap, that connects or connect the cap to the cartridge head in a reversibly detachable manner, wherein a fastening element, that is irreversibly connected or irreversibly connectable to a fastening element of the partition panel, is attached to an inner side of the cap.

20. A method for mixing pasty cement components of a pasty cement dough utilizing the storage and mixing system according to claim 1, the method comprising consecutively:
a) pulling the partition panel out of the cartridge through the cartridge head, wherein the two cavities are connected to one another;
b) removing the cartridge head from the cartridge, or removing at least two plugs from at least two passages in the cartridge head, whereby the cartridge (1) is opened;
c) placing on and connecting a dispensing tube to the opened cartridge, wherein the dispensing tube comprises a mixer;
d) inserting the cartridge into an applicator;
e) pressing out the pasty cement components with the aid of the applicator by axially moving the dispensing plunger in the direction of the dispensing tube, wherein the two cement components are mixed by the mixer in the dispensing tube to produce the pasty cement dough; and
f) pressing the mixed pasty cement dough out of a dispensing opening of the dispensing tube.

21. The method according to claim 20, further comprising:
detaching a connecting element, that connects the cartridge head to the cartridge, so as to remove the cartridge head from the cartridge in b).

22. The method according to claim 20, wherein the dispensing tube is connected to the cartridge by connecting the connecting element of the dispensing tube to a connecting means of the cartridge.

23. The method according to claim 20, further comprising:
driving a rod comprising a plate, serving as parts of the applicator, for pressing the cement components out of the cartridge and into the dispensing tube by way of the applicator, wherein the plate pushes against the dispensing plunger of the storage and mixing system.

24. The method according to claim 20, wherein the partition panel is connected to a cap, and that, in a), the partition panel connected to the cap is pulled completely out of the cartridge toward the outside by pulling the cap or a handle of the cap.

25. The method according to claim 20, wherein the applicator can be driven manually, or can be driven by compressed air or electrically.

* * * * *